United States Patent [19]
Tsou et al.

[11] Patent Number: 6,087,504
[45] Date of Patent: Jul. 11, 2000

[54] PROCESS FOR THE PREPARATION OF 1,1'-DIALKYL-4,4'-BIPYRIDINIUM SALT COMPOUNDS

[75] Inventors: Chiu-Peng Tsou; Sheau-Cheau Lin; Ting-Kai Huang; Chi-Yung Shen, all of Ping-Chen, Taiwan

[73] Assignee: Kuo Ching Chemical Co., Ltd., Taouyan County, Taiwan

[21] Appl. No.: 09/239,761

[22] Filed: Jan. 29, 1999

[51] Int. Cl.$^7$ ...................... C07D 213/22; C07D 213/26
[52] U.S. Cl. ............................................ 546/259; 546/258
[58] Field of Search ..................................... 546/259, 258

[56] References Cited

U.S. PATENT DOCUMENTS

| | | | |
|---|---|---|---|
| 3,755,337 | 8/1973 | Carey | 546/259 |
| 3,787,426 | 1/1974 | Colchester et al. | 546/259 |
| 3,790,585 | 2/1974 | Colchester et al. | 546/259 |
| 3,899,500 | 8/1975 | Colchester et al. | 546/259 |
| 3,905,986 | 9/1975 | Colchester et al. | 546/259 |

*Primary Examiner*—Alan L. Rotman
*Attorney, Agent, or Firm*—Dougherty & Troxell

[57] ABSTRACT

This invention relates to an improved method of preparing 1,1'-dialkyl-4,4'-bipyridinium salt compounds which is free of cyanic ion and contains low amount of inorganic salts.

7 Claims, No Drawings

PROCESS FOR THE PREPARATION OF 1,1'-DIALKYL-4,4'-BIPYRIDINIUM SALT COMPOUNDS

This invention relates to an improved method of preparing 1,1'-dialkyl-4,4'-bipyridinium salt compounds which is free of cyanic ion and contains low amount of inorganic salts.

BACKGROUND OF THE INVENTION

The present invention relates to an improved method of preparing bipyridinium salt by the coupling of 1-alkylpyridinium salt (expressed by the following formula I) with a base in the presence of an alkaline metal cyanide. The reaction mixture is added to a sufficient amount of an aqueous divalent transitional metal salt solution. After the co-precipitated divalent transitional metal cyanide and inorganic salt are filtered off, the filtrate is oxidized to afford 1,1'-dialkyl-4,4'-bipyridinium salt (expressed by the following formula II), free of cyanide ion and with low concentration of inorganic salts.

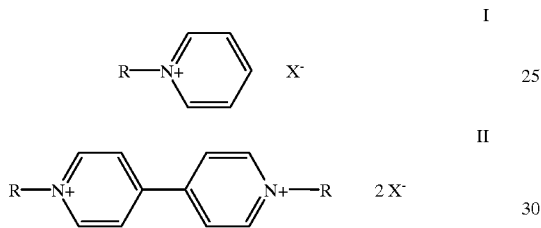

(wherein R denotes an alkyl group having 1 to 10 carbon atoms; X denotes a chlorine atom, bromine atom, or a sulfate group. The compound of formula I, wherein R and X denote methyl group and chlorine atom, respectively, is the well-known pesticide paraquat.)

The preparation of 1,1'-dialkyl-4,4'-bipyridinium salt compounds by the alkaline metal cyanide—catalyzed coupling of 1-alkylpyridinium salts, followed by oxidation, is a published synthesis process. However, a environmentally sound treatment for the removal of the residual cyanides and inorganic salts has not been reported. U.S. Pat. Nos. 3,723,444; 3,787,426; 3,793,335; 3,868,381; 3,899,500; 3,905,986 disclose the preparation of 1,1'-dialkyl-4,4'-bipyridinium salt by reacting 1-alkylpyridinium salt with an soluble acid accepting agent (i.e. sodium hydroxide) in an organic solvent containing 5 to 50% of water at the presence of at least two equivalents of sodium cyanide. Such processes are uneconomical and inefficient on a commercial scale. For instance, the patents quoted above mention the of soluble alkaline metal salts of 4,4'-diamino-distyrene-2,2'-disulfonic acid (amsonic acid), with which the 1,1'-dialkyl-4,4'-bipyridinium cation is precipitated as an acidic salt and separated from cyanides by filtration. The salts are further treated with ion exchanged process to remove residual cyanic ions in order to afford a qualified product. Yet this is a very sophisticated and costly treatment process.

One other example discloses the addition of ferrous sulfate hydrate to the aqueous solution of 1,1'-dialkyl-4,4'-bipyridinium cation to precipitate cyanides, which are then removed by filtration. However, this process results in low yield of the final product. Another example discloses the extraction of the coupled precursor of 1,1'-dialkyl-4,4'-bipyridinium salt with an organic solvent such as toluene. The cyanic ion containing aqueous layer is phase separated, and the organic layer is then oxidized to give the 1,1'-dialkyl-4,4'-bipyridinium salt. Yet this process has the disadvantages of low recovery rate and cyanic ion-containing waste water.

In the present invention, the applicant has proposed a method of preparing 1,1'-dialkyl-4,4'-bipyridinium salt (formula II) by the coupling of 1-alkylpyridinium salt (formula I) in the presence of a proper amount of a cyanide and a base to afford the precursor of bipyridinium salt. The precursor is further oxidized to give the title compound in high yield. The applicant has further proposed a method of isolating the precursor by salting out the cyanide and inorganic salts in an aqueous solution of divalent transitional metal salt.

SUMMARY OF THE INVENTION

The present invention provides a process for the preparation of 1,1'-dialkyl-4,4'-bipyridinium salt compounds, comprising the steps as follows:

a) by the coupling of 1-alkylpyridinium salt (formula I) with a base in the presence of an alkaline metal cyanide in an organic solvent;

b) filtering off the cyanide as divalent transitional metal cyanide by quenching the reaction mixture in step (a) with an aqueous solution of divalent transitional metal salt;

c) oxidation of the filtrate in step (b) with a suitable oxidation reagent to afford the 1,1'-dialkyl-4,4'-bipyridinium salt (formula II) compounds.

DETAILED DESCRIPTION OF THE INVENTION

It is an object of the present invention to provide a method which can resolve all the problems encountered in conventional methods of preparing 1,1'-dialkyl-4,4'-bipyridinium salt compounds.

It is another object of the present invention to provide a method to isolate the cyanic ion for recycle purpose or other applications.

The inventors therefore have conducted various investigations with a view to resolving the above described problem by isolating the cyanic ion and organic salts before the oxidation is carried out. It has been found that an aqueous solution of divalent transitional metal salt added into the reaction medium can force the cyanic ion to precipitate as a divalent transitional metal cyanide due to common ion effect. After filtration, the filtrate is oxidized with a suitable oxidation reagent to afford the 1,1'-dialkyl-4,4'-bipyridinium salt free of cyanic ion and with low concentration of inorganic salts.

The starting material 1-alkylpyridinium salt can be expressed by formula I:

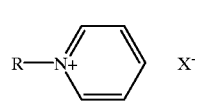

wherein R denotes an alkyl group having 1 to 10 carbon atoms, In particular a methyl group; X denotes a chlorine atom, bromine atom, or a sulfate group.

The cyanide catalyst refers to sodium cyanide, potassium cyanide and the like, in particular sodium cyanide. The amount of such cyanides may be 0.5 to 4.0 equivalents, preferably more than 2.0 equivalents.

The base refers to sodium hydroxide, potassium hydroxide, calcium hydroxide, sodium carbonate, potassium carbonate, ammonia, sodium methoxide and the like.

The organic solvent refers to 75–95% aqueous solution of methanol, ethanol, or isopropanol; N,N-dimethylformamide and the like.

The divalent transitional metal salt refers to zinc chloride, zinc sulfate, copper dichloride, copper sulfate and the like, in particular zinc chloride.

The suitable oxidation reagent refers to chlorine, oxygen, air, sulfuryl chloride, or sulfur dioxide, in particular chlorine. The target product 1,1'-dialkyl-4,4'-bipyridinium salt can be expressed by formula II:

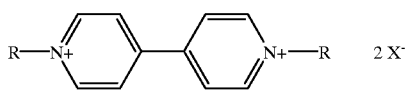

wherein R denotes an alkyl group having 1 to 10 carbon atoms, in particular a methyl group.

DESCRIPTION OF THE PREFERED EMBODIMENTS

The following embodiments are to be construed merely to illustrate the objects, characters, and effects of the present invention. Various modifications of these embodiments in addition to those shown and described therein will become apparent to those skilled in the art, and are also intended to fall within the scope of the invention. The embodiments of the invention in which an exclusive property or privilege is claimed are defined in the appended claims.

EXAMPLE 1

Sodium cyanide (120.5 g, 2.5 mole) and sodium hydroxide (48.0 g, 1.2 mole) were added to a solution of 1-methylpyridinium hydrochloride (129.5 g, 1.0 mole) in 90% aqueous denatured alcohol (1000 ml) under nitrogen at room temperature. The reaction mixture was heated to reflux for 30 minutes. The reaction followed by TLC until the disappearance of 1-methylpyridinium hydrochloride.

After cooled to room temperature, the reaction mixture was quenched with an aqueous solution of zinc chloride (190.4 g, 1.4 mole) in 50 ml water and stirred for 30 minutes. The mixture was kept at room temperature without stirring for one hour to allow the complete precipitation of inorganic salts. The inorganic salts were filtered and washed with denatured alcohol (150 ml). The combined filtrate, of which the pH was adjusted to 4–6 with hydrochloric acid, was oxidized with oxygen at below 50° C. until the solution turned from dark purple to tan. The solvent was the distilled to give 291.8 g of 1,1' dimethyl-4,4'-bipyridinium salt solution as a yellow-green oil (42% content, 97.5% of HPLC purity). The conversion yield was 93%; there was no cyanic ion present after analysis.

Data for final product: $^1$H NMR (300 MHz, $D_2O$) δ9.04 (d, 2H, J=6.6 Hz), 8.52 (d, 2H, J=6.6 Hz), 4.47 (s, 3H). The inorganic salts recovered in the procedure weighed 558.5 g and contained predominantly $Zn^{+2}$, $CN^-$, $Na^+$ and $Cl^-$.

EXAMPLE 2

Sodium cyanide (120.5 g, 2.5 mole) and sodium hydroxide (48.0 g, 1.2 mole) were added to a solution of 1-methylpyridinium hydrochloride (129.5 g, 1.0 mole) in 90% aqueous denatured alcohol (1000 ml) under nitrogen at room temperature. The reaction mixture was heated to reflux for 30 minutes. The reaction followed by TLC until the disappearance of 1-methylpyridinium hydrochloride.

After cooled to room temperature, the reaction mixture was quenched with a aqueous solution of $ZnSO_4.7H_2O$ (401.8 g, 1.4 mole) in 250 ml water was added and stirred for 30 minutes. The mixture was kept at room temperature without stirring for one hour to allow the complete precipitation of inorganic salts. The inorganic salts were filtered and washed with denatured alcohol (150 ml). The combined filtrate, of which the pH was adjusted to 4–6 with hydrochloric acid, was oxidized with oxygen at below 50° C. until the solution turned from dark purple to tan. The solvent was the distilled to give 345.4 g of 1,1' dimethyl-4,4'-bipyridinium salt solution as a yellow-green oil (28% content, 97% of HPLC purity). The conversion yield was 73%, there was no cyanic ion present after analysis.

Data for final product: $^1$H NMR (300 MHz, $D_2O$) δ9.04 (d, 2H, J=6.6 Hz), 8.52 (d, 2H, J=6.6 Hz), 4.47 (s, 3H). The inorganic salts recovered in the procedure weighed 492.5 g and contained predominantly $Zn^{+2}$, $Na^+$, $CN^-$, $SO_4^{-2}$ and $Cl^-$.

EXAMPLE 3–6

Example 1 is repeated, except that the reaction was treated with different oxidants instead of oxygen/HCl. The conversion yield of each experiment is shown as follows:

| example | Oxidant | Conversion yield |
| --- | --- | --- |
| 3 | $Cl_2$ | 93% |
| 4 | $SO_2Cl_2$ | 90% |
| 5 | $SO_2$ | 83% |
| 6 | Air/HCl | 78% |

What is claimed is:

1. An improved process for the preparation of 1,1'-dialkyl-4,4'-bipyridinium salt of the formula II:

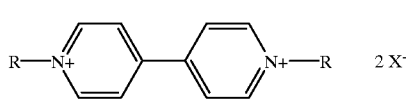

wherein R is an alkyl group having 1 to 10 carbon atoms; X is a chlorine atom, bromine atom, or a sulfate group, comprising the steps:

(1) by the coupling of 1-alkylpyridinium salt with a base in the presence of an alkaline metal cyanide in an organic solvent;

(2) filtering off the cyanide as divalent transitional metal cyanide by quenching the reaction mixture in step (1) with an aqueous solution of divalent transitional metal salt; and (3) oxidation of the filtrate in step (2) with suitable oxidation reagent to afford the 1,1'-dialkyl-4,4'-bipyridinium salt.

2. A process according to claim 1, wherein the alkaline metal cyanide is potassium cyanide or sodium cyanide.

3. A process according to claim 1, wherein the base is selected from the group consisting of sodium hydroxide, potassium hydroxide, sodium carbonate, potassium carbonate, ammonia and sodium methoxide.

4. A process according to claim 1, wherein the organic solvent is selected from the group consisting of 75–95% aqueous solution of methanol, ethanol, isopropanol and N,N-dimethylformamide.

5. A process according to claim 1, wherein the divalent transitional metal salt is selected from the group consisting of zinc chloride, zinc sulfate, copper dichloride and copper sulfate.

6. A process according to claim 1, wherein the divalent transitional metal cyanide is zinc cyanide or copper cyanide.

7. A process according to claim 1, wherein the oxidant is selected from the group consisting of: chlorine, oxygen, air, sulfuryl chloride and sulfur dioxide.

* * * * *